United States Patent
Mehta

(10) Patent No.: US 11,225,513 B2
(45) Date of Patent: *Jan. 18, 2022

(54) METHOD TO IMPROVE VIRUS FILTRATION CAPACITY

(71) Applicant: Genentech, Inc., South San Francisco, CA (US)

(72) Inventor: Amit Mehta, Fremont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,564

(22) Filed: Apr. 14, 2020

(65) Prior Publication Data

US 2020/0347118 A1 Nov. 5, 2020

Related U.S. Application Data

(63) Continuation of application No. 12/806,171, filed on Aug. 6, 2010, now Pat. No. 10,662,237.

(60) Provisional application No. 61/231,811, filed on Aug. 6, 2009.

(51) Int. Cl.
*C07K 1/36* (2006.01)
*C07K 1/18* (2006.01)
*C07K 1/34* (2006.01)
*C07K 16/06* (2006.01)

(52) U.S. Cl.
CPC .............. *C07K 16/065* (2013.01); *C07K 1/18* (2013.01); *C07K 1/34* (2013.01); *C07K 1/36* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel | |
| 4,676,980 A | 6/1987 | Segal | |
| 4,816,567 A | 3/1989 | Cabilly | |
| 4,975,278 A | 12/1990 | Senter | |
| 5,500,362 A | 3/1996 | Robinson | |
| 5,545,806 A | 8/1996 | Lonberg et al. | |
| 5,545,807 A | 8/1996 | Surani | |
| 5,569,825 A | 10/1996 | Lonberg | |
| 5,591,828 A | 1/1997 | Bosslet | |
| 5,625,126 A | 4/1997 | Ladner et al. | |
| 5,629,084 A | 5/1997 | Moya | |
| 5,633,425 A | 5/1997 | Lonberg et al. | |
| 5,641,870 A | 6/1997 | Rinderknecht | |
| 5,661,016 A | 8/1997 | Lonberg et al. | |
| 5,821,337 A | 10/1998 | Carter | |
| 6,008,036 A | 12/1999 | Fanget | |
| 6,177,548 B1 | 1/2001 | Wan | |
| 7,001,550 B2 | 2/2006 | Van Reis | |
| 7,118,675 B2 | 10/2006 | Siwak | |
| 7,847,071 B2 | 12/2010 | Bonnerjea | |
| 8,067,549 B2 | 11/2011 | Sabbadini | |
| 10,662,237 B2 | 5/2020 | Mehta | |
| 2002/0151688 A1 | 10/2002 | Ristol | |
| 2003/0036638 A1 | 2/2003 | Joergensen | |
| 2003/0146156 A1 | 8/2003 | Siwak | |
| 2003/0229212 A1 | 12/2003 | Fahrner | |
| 2004/0116676 A1 | 6/2004 | Hotta | |
| 2004/0241878 A1 | 12/2004 | Thommes | |
| 2006/0257972 A1 | 11/2006 | Ishihara | |
| 2007/0014724 A1 | 1/2007 | Witte | |
| 2009/0148443 A1 | 6/2009 | Sabbadini | |
| 2011/0034674 A1 | 2/2011 | Mehta | |
| 2011/0137012 A1 | 6/2011 | Katayama | |
| 2014/0287026 A1 | 9/2014 | Kuhne | |

FOREIGN PATENT DOCUMENTS

| | | |
|---|---|---|
| CN | 101437839 A | 5/2009 |
| EP | 0308936 A2 | 2/1989 |
| EP | 0308936 B1 | 3/1989 |
| EP | 0308936 A3 | 2/1990 |
| EP | 0404097 A2 | 12/1990 |
| EP | 1403274 A1 | 3/2004 |
| EP | 1577319 A1 | 9/2005 |
| EP | 1614693 A1 | 1/2006 |
| EP | 2281000 A2 | 2/2011 |
| EP | 2435474 A2 | 4/2012 |
| EP | 2473617 A1 | 7/2012 |
| JP | H02198687 A | 8/1990 |
| JP | H03008759 A | 1/1991 |
| JP | H07116484 A | 5/1995 |
| JP | H07265691 A | 10/1995 |
| JP | H11509554 A | 8/1999 |
| JP | 2002541155 A | 12/2002 |
| JP | 2003002896 A | 1/2003 |
| JP | 2006249082 A | 9/2006 |
| JP | 2006522830 A | 10/2006 |
| JP | 2008500959 A | 1/2008 |

(Continued)

OTHER PUBLICATIONS

Abe, H. et al. (2000, e-pub. Jul. 11, 2009). "Removal of Parvovirus B19 From Hemoglobin Solution by Nanofiltration," Artif. Cells, Blood Substit Immobil. Biotechnol 28(5):375-383.

AMERSHAM Biosciences Antibody Purification Handbook, (2002), 112 pages.

Bakhshayeshi, M. et al. (2007, e-pub. Dec. 13, 2007). "Effect of Solution pH on Protein Transmission and Membrane Capacity During Virus Filtration," Biotechnol. Bioeng. 100(1):108-117.

Berting, A. et al. (2005). "Effective Poxvirus Removal By Sterile Filtration During Manufacture of Plasma Derivatives," Journal of Medical Virology 75:603-607.

(Continued)

*Primary Examiner* — Benjamin P Blumel
(74) *Attorney, Agent, or Firm* — Morrison & Foerster LLP

(57) ABSTRACT

The present invention relates to the field of protein purification. In particular, the invention concerns methods for increasing the filtration capacity of virus filters, by combined use of endotoxin removal and cation-exchange media in the prefiltration process.

18 Claims, 4 Drawing Sheets

(56) References Cited

FOREIGN PATENT DOCUMENTS

| | | |
|---|---|---|
| RU | 2145873 C1 | 2/2000 |
| WO | WO198101145 A1 | 4/1981 |
| WO | WO198807378 A1 | 10/1988 |
| WO | WO198905859 A1 | 6/1989 |
| WO | WO199100360 A1 | 1/1991 |
| WO | WO199220373 A1 | 11/1992 |
| WO | WO199308829 A1 | 5/1993 |
| WO | WO199311161 A1 | 6/1993 |
| WO | WO199404690 A1 | 3/1994 |
| WO | WO199508574 A1 | 3/1995 |
| WO | WO199627011 A1 | 9/1996 |
| WO | WO200059927 A1 | 10/2000 |
| WO | WO2003066669 A2 | 8/2003 |
| WO | WO2003066669 A3 | 12/2003 |
| WO | WO2003102132 A2 | 12/2003 |
| WO | WO2003102132 A3 | 10/2004 |
| WO | WO2004091510 A2 | 10/2004 |
| WO | WO2005073252 A1 | 8/2005 |
| WO | WO2005073367 A1 | 8/2005 |
| WO | WO2004091510 A3 | 2/2006 |
| WO | WO2006042541 A1 | 4/2006 |
| WO | WO2006096489 A2 | 9/2006 |
| WO | WO2006096489 A3 | 3/2007 |
| WO | WO2007108955 A1 | 9/2007 |
| WO | WO2007129895 A2 | 11/2007 |
| WO | WO2008025747 A1 | 3/2008 |
| WO | WO2008036899 A2 | 3/2008 |
| WO | WO2008036899 A3 | 5/2008 |
| WO | WO2008063892 A2 | 5/2008 |
| WO | WO2008073620 A2 | 6/2008 |
| WO | WO2008063892 A3 | 8/2008 |
| WO | WO2008136398 A1 | 11/2008 |
| WO | WO2007129895 A3 | 12/2008 |
| WO | WO2009017491 A1 | 2/2009 |
| WO | WO2008073620 A3 | 5/2009 |
| WO | WO2009085765 A1 | 7/2009 |
| WO | WO2009138484 A2 | 11/2009 |
| WO | WO2009138484 A3 | 1/2010 |
| WO | 2010109920 A1 | 9/2010 |
| WO | WO2010138736 A2 | 12/2010 |
| WO | WO2010138736 A3 | 3/2011 |
| WO | WO2011028753 A1 | 3/2011 |

OTHER PUBLICATIONS

Boerner, P. et al. (Jul. 1, 1991). "Production of Antigen-Specific Human Monoclonal Antibodies From in Vitro-Primed Human Splenocytes," J. Immunol. 147(1):86-95.

Bohonak, D.M. et al. (2005, e-pub. Feb. 12, 2005). "Compaction And Permeability Effects With Virus Filtration Membranes," J. of Membrane Science 254:71-79.

Bolton, G. et al. (2005). "Normal-flow Virus Filtration: Detection And Assessment of The Endpoint In Bioprocessing," Biotechnol. Appl. Biochem. 42:133-142.

Bolton, G.R. et al. (2006). "Increasing The Capacity of Parvovirus-Retentive Membranes: Performance of The Viresolve™ Prefilter," Biotechnol. Appl. Biochem. 43:55-63.

Brennan, M. et al. (Jul. 5, 1985). "Preparation of Bispecific Antibodies by Chemical Recombination of Monoclonal Immunoglobulin G1 Fragments," Science 229:81-83.

Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.

Brown, A. et al. (Jul. 1, 2010, e-pub. Mar. 12, 2010). "Increasing Parvovirus Filter Throughput of Monoclonal Antibodies Using Ion Exchange Membrane Adsorptive Pre-Filtration," Biotechnology and Bioengineering 106(4):627-637.

Brown, A. et al. (Mar. 14, 2008). "Use of Charged Membranes To Identify Soluble Protein Foulants In Order To Facilitate Parvovirus Filtration," IBC's 20th Antibody Development and Production conference, San Diego, CA. 38 pages.

Brown, F. (1993). "Review of Accidents Caused By Incomplete Inactivation of Viruses," Dev. Biol. Stand. 81:103-107.

Brüggermann, M. et al. (1993). "Designer Mice: The Production Of Human Antibody Repertoires In Transgenic Animals," Year Immunology 7:33-40.

Burnouf, T. et al. (2005). "Place of Nanofiltration for Assuring Viral Safety of Biologicals," Current Nanoscience 1:189-201.

Capel, P.J. et al. (Feb. 1994). "Heterogeneity of Human IgG Fc receptors," Immunomethods 4(1):25-34.

Carter, P. et al. (May 1992). "Humanization of An Anti-p185HER2 Antibody For Human Cancer Therapy," Proc. Natl. Acad. Sci. USA 89:4285-4289.

Chen, R.H. et al. (2009, e-pub. Oct. 22, 2018). "Factors affecting Endotoxin Removal From Recombinant Therapeutic Proteins By Anion Exchange Chromatography," Protein Expression and Purification 64(1):76-81.

CHMP Assessment Report for Stelara, European Medicines Agency, Procedure No. EMEA/H/C/000958, (2009), 58 pages.

Chothia, C. et al. (Aug. 20, 1987). "Canonical Structures for the Hypervariable Regions of Immunoglobulins," J. Mol. Biol. 196(4):901-917.

Chu, L. et al. (2001). "Industrial Choices For Protein Production By Large-Scale Cell Culture," Current Opinion in Biotechnology 12:180-187.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. U.S.A. 95:652-656.

Cole, S.P.C. et al. (1985). "The EBV-Hybridoma Technique and its Application to Human Lung Cancer," Monoclonal Antibodies and Cancer Therapy, Alan R. Liss, Inc., New York, New York, pp. 77-96.

Curtis, S. et al. (2003). "Generic/Matrix Evaluation of SV40 Clearance By Anion Exchange Chromatography In Flow Through Mode," Biotechnology and Bioengineering 84(2):179-186.

Daëron, M. (1997). "Fc Receptor Biology," Ann. Rev. Immunol. 15:203-234.

De Haas, M. et al. (1995). "Fcγ Receptor of Phagocytes," J. Lab. Clin. Med. 126(4):330-341.

DOW Liquid Separations, DOWEX Ion Exchange Resins—Fundamentals of Ion Exchange, (Jun. 2000), pp. 1-9.

European Register of European Patent Application No. 10722883.5, (dated 2018), 4 pages.

Excerpts from Textbook Gottschalk, Uwe, ed. "Process Scale Purification of Antibodies," Chapters 1-3, 5, 7, 8, 9), No. 577.27 PRO. Hoboken, NJ. John Wiley & Sons, (Feb. 2009), 172 pages.

Fahrner, R.L. et al. (2001, e-pub. Apr. 15, 2018). "Industrial Purification of Pharmaceutical Antibodies Development, Operation, and Validation of Chromatography Processes," Biotechnol. Genet. Eng. Rev. 18:301-327.

Fishwild, D.M. et al. (1996). "High-Avidity Human IgGK Monclonal Antibodies From a Novel Strain of Minilocus Transgenic Mice," Nature Biotechnology 14:845-851.

Furuya, K. et al. (2006, e-pub. May 16, 2006). "Implementations of A 20-nm Pore-Size Filter In The Plasma Derived Factor VIII Manufacturing Process,". Vox Sanguinis 91:119-125.

Gagnon, P. et al. (2007). "Chapter 17 in Polishing Methods for Monoclonal IgG Purification," pp. 491-505.

Gagnon, P. et al. (2009). "Monoclonal Antibody Purification With Hydroxyapatite," New Biotechnology 25(5):287-293.

Gagnon, P. et al. (Feb. 1, 2006). "A Ceramic Hydroxyapatite Based Purification Platform. Simultaneous Removal of Leached Protein A, Aggregates, DNA and Endotoxins from Mabs," BioProcess International 4:50-60, 8 pages.

Garnick, RL. (1998). "Raw Materials as A Source Of Contamination In Large-Scale Cell Culture," Dev. Biol. Stand. 93:21-29.

Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.

Ghose, S. et al. (2007). "Chapter 16: Protein A Affinity Chromatography for Capture and Purification of Monoclonal Antibodies

(56) References Cited

OTHER PUBLICATIONS and Fc-Fusion Proteins: Practical Consideration for Process Development," in Process Scale Bioseparations for the Biopharmaceutical Industry, pp. 463-489.

Ghose, S. et al. (2009). "Integrated Polishing Steps for Monoclonal Antibody Purification," Chapter 7 in Process Scale Purification of Antibodies, U. Gottschalk (Ed). pp. 145-167.

Giovannoni, L. et al. (Dec. 2008). "Antibody Purification Using Membrane Absorbers," BioPharm. Int. 21 (12):48-52.

Goding, J.W. (1986). "Production of Monoclonal Antibodies," Chapter 3 in Monoclonal Antibodies: Principles and Practice, Academic Press, New York, pp. 59-103.

Gottschalk, U. (2008). "Bioseparation in Antibody Manufacturing: The Good, The Bad, and the Ugly," Biotechnol. Prog. 24(3):496-503.

Gottschalk, U. (2008). "Downstream Processing," in Filtration and Purification in the Biopharmaceutical Industry, Jornitz M. W. and Meltzer, T.H. pp. 459-493.

Gottschalk, U. (Jun. 1, 2005). "Downstream Processing of Monoclonal Antibodies: From High Dilution to High Purity," BioPharm International 18(6):1-11.

Graham, F.L. et al. (Apr. 1973). "A New Technique for the Assay of Infectivity of Human Adenovirus 5 DNA," Virology 52(2):456-467.

GRAVER Technologies Powdex® Selection Guide, 2 pages, (Apr. 2002).

Gruber, M. et al. (1994). "Efficient Tumor Cell Lysis Mediated by a Bispecific Single Chain Antibody Expressed in *Escherichia coli*," J. Immunol. 152:5368-5374.

Guyer, R.L. et al. (Aug. 1976). "Immunoglobulin Binding By Mouse Intestinal Epithelial Cell Receptors," J. Immunol. 117(2):587-593.

Henrie, M. et al. (2008). "In Vitro Assessment of Dialysis Membrane as an Endotoxin Transfer Barrier: Geometry, Morphology, and Permeability," Artificial Organs 9:701-710.

Hirasaki, T. et al. (1994). "Mechanism of Removing Japanese Encephalitis Virus (JEV) and Gold Particles Using Cuprammonium Regenerated Cellulose Hollow Fiber (i-BMM or BMM) From Aqueous Solution Containing Protein," Polymer Journal 26(11):1244-1256.

Hoffmann, H. et al. Mar. 2-3, 2009). Outsourcing Manufacturing of Biopharmaceuticals, 20 pages.

Holliger, P. et al. (Jul. 1993). "Diabodies": Small Bivalent and Bispecific Antibody Fragments, Proc. Natl. Acad. Sci. USA 90:6444-6448.

Hoogenboom, H.R. et al. (1992). "By-Passing Immunisation. Human Antibodies From Synthetic Repertoires of Germline VH Gene Segments Rearranged in Vitro," J. Mol. Biol. 227:381-388.

International Preliminary Report on Patentability, dated Feb. 7, 2012, for PCT Application No. PCT/US2010/044760, filed Aug. 6, 2010, 6 pages.

International Search Report, dated Nov. 12, 2010, for PCT Application No. PCT/US2010/044760, filed Aug. 6, 2010, 3 pages.

Ireland, T. et al. (Nov. 2005). "Optimizing Virus Filter Performance With Prefiltration," BioProcess Int. 3(Suppl. 10):S44-S47.

Ishihara, T. et al. (2007, e-pub. Nov. 7, 2007). "Accelerated Purification Process Development of Monoclonal Antibodies for Shortening Time to Clinic Design and Case Study of Chromatography Processes," J. of Chromatography A. 1176:149-156.

Jakobovits, A. et al. (Mar. 18, 1993). "Germ-Line Transmission and Expression of a Human-Derived Yeast Artificial Chromosome," Nature 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.

Jones, P.T. et al. (May 29, 1986). "Replacing the Complementarity-Determining Regions in a Human Antibody With Those From a Mouse," Nature 321:522-525.

Kastner, M. (2000). Protein Liquid Chromatography vol. 61 Elsevier Table 1.5, p. 21, 2 pages.

Katz, A. et al. (2016). "Prefilration and Process Improvements: Enhancing Virus Filter Performance With The Use of Adsorptive Depth or Surface Modified Prefilters," 1 page.

Kelley, B. et al. (2009, e-pub Aug. 15, 2009). "Downstream Processing of Monoclonal Antibodies: Current Practices and Future Opportunities," in Process Scale Purification of Antibodies edited by Uwe Gottschalk John Wiley & Sons, Inc. pp. 1-23.

Kelley, B. et al. (Sep./Oct. 2009, e-pub. Sep. 1, 2009). "Industrialization of mAb Production Technology: The Bioprocessing Industry at a Crossroads," mAbs 1(5):443-452.

Kern, G. et al. (Oct. 1, 2006). "Virus Removal by Filtration: Points to Consider," BioPharm. Int. 19(10): 1-6.

Kim, I.N. et al. (2009). "Removal and Inactivation of Viruses During the Manufacture of a High-Purity Antihemophilic Factor IX From Human Plasma," Biotechnology and Bioprocess Engineering 14:716-724.

Kim, J-K. et al. (1994). "Localization of the Site of the Murine IgGI Molecule That is Involved in Binding to the Murine Intestinal Fc Receptor," Eur. J. Immunol. 24:2429-2434.

Kostelny, S.A. et al. (Mar. 1, 1992). "Formation of a Bispecific Antibody By The Use of Leucine Zippers," J. Immunol. 148(5):1547-1553.

Kozbor, D. (Dec. 1984). "A Human Hybrid Myeloma for Production of Human Monoclonal Antibodies," J. Immunol. 133(6):3001-3005.

Köhler, G. et al. (Aug. 7, 1975). "Continuous Cultures of Fused Cells Secreting Antibody of Predefined Specificity," Nature 256:495-497.

Levy, R.V. et al. (1998). "Filtration and Removal of Viruses From Biopharmaceuticals," Meltzer and Jornitz eds. Marcel Dekker, New York pp. 619-646.

Li, F. et al. (Sep./Oct. 2005). "Current Therapeutic Antibody Production and Process Optimization," BioProcessing J. 4(5):1-8.

Li, Y. et al. (2009). "Development of a Platform Process for the Purification of Therapeutic Monoclonal Antibodies," Chapter 9 in Process Scale Purification of Antibodies. U. Gottschalk (ed.) pp. 187-201.

Lieber, M.M. et al. (1973). "Mammalian Cells In Culture Frequently Release Type C Viruses," Science 182:56-59.

Liu, H. et al. (Sep./Oct. 2019). "Recovery and Purification Process Development for Monoclonal Antibody Productio," mAbs 2(5): 480-499.

Lonberg, N. et al. (Apr. 28, 1994). "Antigen-Specific Human Antibodies From Mice Comprising Four Distinct Genetic Modifications," Nature 368:856-859.

Lonberg, N. et al. (1995). "Human Antibodies From Transgenic Mice," Intern. Rev. Immunol. 13:65-93.

Lubiniecki, A.S. et al. (1989). "Endogenous Retroviruses Of Continuous Cell Substrates," Develop. Biol. Standard 70:187-189.

Lute, S. et al. (2004). "Characterization of Coliphage PR772 and Evaluation of Its Use for Virus Filter Performance Testing," Applied and Environmental Microbiology 70(8):4864-4871.

Magalhães, P.O. (May 18, 2007). "Methods of Endotoxin Removal From Biological Preparations: A Review," J. Pharm. Pharmaceut. Sci. 10(3):388-404.

Marks, J.D. et al. (1991). "By-Passing Immunization. Human Antibodies From V-Gene Libraries Displayed on Phage," J. Mol. Biol. 222:581-597.

Marks, J.D. et al. (Jul. 1992). "By-Passing Immunization: Building High Affinity Human Antibodies by Chain Shuffling," Bio/Technology 10: 779-783.

Massey, R.J. (Jul. 1987). "Catalytic antibodies catching on," Nature 328:457-458.

McCafferty, J. et al. (Dec. 6, 1990). "Phage Antibodies: Filamentous Phage Displaying Antibody Variable Domains," Nature 348:552-554.

Metha, A. et al. (May 2008) "Purifying Therapeutic Monoclonal Antibodies," Chemical Engineering Progress (CEP) 104(5):S14-S20.

MILLIPORE Corporation, Millistak+® Pod Disposable Depth Filter System, (Apr. 2009), pp. 1-4.

(56) References Cited

OTHER PUBLICATIONS

MILLIPORE Corporation, Optimizing Viral Clearance Processes-Ensuring Product Quality, Yield and Safety Using Viresolve NFP Filters, Billerica, MA, Millipore Corporation (Dec. 2003), 4 pages.
Milstein, C. et al. (Oct. 6, 1983). "Hybrid Hybridomas and Their Use In Immunohistochemistry," Nature 305:537-540.
Morrison, S.L. (Apr. 28, 1994). "Success in Specification," Nature 368:812-813.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Motoyama, A. et al. (May 2007, e-pub. Apr. 6, 2007). "Anion and Cation Mixed-Bed Ion Exchange for Enhanced Multidimensional Separations of Peptides and Phosphopeptides," Analytical Chemistry 79(10):3623-3634, Abstract Only.
Munson, P.J. et al. (1980). "LIGAND: A Versatile Computerized Approach for Characterization of Ligand-Binding Systems," Anal. Biochem. 107:220-239.
Neuberger, M. (Jul. 1996). "Generating High-Avidity Human Mabs in Mice," Nature Biotechnol. 14:826.
Neuberger, M.S. et al. (Dec. 13, 1984). "Recombinant antibodies processing novel effector functions," Nature 312:604-608.
Omar, A. et al. (2002). "Removal Of Neutralized Model Parvoviruses And Enteroviruses In Human IgG Solutions By Nanofiltration," Transfusion 42(8):1005-1010.
Opposition Against European Patent 2 462 158 on Behalf of Bayer Intellectual Property et al., dated Oct. 10, 2018, 66 pages.
Opposition Against European Patent 2 462 158 on Behalf of Griinecker Patent et al., dated Oct. 10, 2018, 40 pages.
Opposition Against European Patent 2 462 158 on Behalf of John Gerard Leeming, dated Oct. 10, 2018, 28 pages.
Opposition Against European Patent 2 462 158 on Behalf of Konig S. Tilmann von Renesse, dated Oct. 10, 2018, 57 pages.
Opposition Against European Patent 2 462 158 on Behalf of Maiwald Patentanwaits et al., dated Oct. 10, 2018, 21 pages.
Opposition Against European Patent 2 462 158 on Behalf of Michalski Httermann & Partner, dated Oct. 10, 2018, 37 pages.
Opposition Against European Patent 2 462 158 on Behalf of Morphosys AG, dated Oct. 10, 2018, 12 pages.
Opposition Against European Patent 2 462 158 on Behalf of Potter Clarkson LLP, dated Oct. 10, 2018, 57 pages.
Opposition Against European Patent 2 462 158 on Behalf of Regina Neuefeind, dated Oct. 10, 2018, 27 pages.
Opposition Against European Patent 2 462 158 on Behalf of Sandra Pohlman, dated Oct. 10, 2018, 34 pages.
Opposition Against European Patent 2 462 158 on Behalf of Strawman LTD, dated Oct. 10, 2018, 20 pages.
Patentee Letter of Dec. 16, 2015, 6 pages.
Pattison, J.R. et al. (1996). "Chapter 64: Parvoviruses" in Baron, S. ed. Medical Microbiology, 4th edition. University of Texas Medical Branch at Galveston, 5 pages.
Pluckthün, A. (1994) "Antibodies from *Escherichia coli*," The Pharmacology of Monoclonal Antibodies pp. 269-315.
Plückthun, A. (1992). "Mono- and Bivalent Antibody Fragments Produced in *Escherichia coli*: Engineering, Folding and Antigen Binding," Immunol. Revs. 130:151-188.
Polylc, Inc. Mixed-Bed Ion-Exchange of Proteins Columbia, MD, PolyLC, Inc. (Feb. 2008), 2 pages.
Presta, L.G. (1992). "Antibody Engineering," Current Opinion in Structural Biology 2:593-596.
Presta, L.G. et al. (Sep. 1, 1993). "Humanization of an Antibody Directed Against IgE," J. Immunol. 151 (5):2623-2632.
Product Information on Viresolve® Pro+ Solution: The Viresolve Shield Prefilter Device, (2006), 2 pages.
Proof of Publication for Powdex® Selection Guide, Wayback Capture Jul. 20-29, 2006, 2 pages.
Proof of Publication for "Process Scale Purification of Antibodies," Chapters 1,5, 7, 8, 9), No. 577.27 PRO, (2009), 8 pages.
Ravetch, J.V. et al. (1991). "Fc Receptors," Annu. Rev. Immunol. 9:457-492.
Recordation Form and Assignment Documents, (2010), 3 pages.
Riechmann, L. et al. (Mar. 24, 1988). "Reshaping Human Antibodies for Therapy," Nature 332:323-327.
Riordan, W.T. et al. (2006, e-pub. Sep. 2, 2009). "Salt Tolerant Membrane Adsorbers for Robust Impurity Clearance," Biotechnol. Prog. 25(6):1695-1702.
Sartorius Stedium Biotech, Technical Note on Virus Purification and Removal https://sartorius.com/mediafile/Appl_Sartobind_Virus_Purification_Removal_SL-4038-e.pdf, 4 pages, (2015).
Shalaby, M.R. et al. (Jan. 1, 1992). "Development of Humanized Bispecific Antibodies Reactive With Cytotoxic Lymphocytes and Tumor Cells Overexpressing the HER2 Protooncogene," J. Exp. Med. 175:217-225.
Shaw, C.H. et.al. (Sep. 1983). "A General Method for the Transfer of Cloned Genes to Plant Cells," Gene 23 (3):315-330.
Shukla, A.A. et al. (2007, e-pub. Oct. 13, 2006). "Downstream Processing of Monoclonal Antibodies-Application of Platform Approaches," Journal of Chromatography B 848(1):28-39.
Sims, M.J. et al. (Aug. 15, 1993). "A Humanized CD18 Antibody Can Block Function Withoud Cell Destruction," J. Immunol. 151:2296-2308.
Skerra, A. (1993). "Bacterial Expression of Immunoglobulin Fragments," Curr. Opinion in Immunol. 5:256-262.
Sommerfeld, S. et al. (2005). "Challenges in Biotechnology Production-Generic Processes and Process Optimization for Monoclonal Antibodies," Chem. Eng. 44:1123-1137.
Stedman's Medical Dictionary, 27th edition, (2000), 4 pages.
Suresh, M.R. et al. (1986). "Bispecific Monoclonal Antibodies From Hybrid Hybridomas," Methods in Enzymology 121:210-228, 19 pages.
Svec, F. et al. eds. (2003). Monolithic Materials: Preparation, Properties, and Applications vol. 67, Elsevier, Table 10.1, p. 216, 2 pages.
Thomas, D.P. (1994). "Viral Contamination of Blood Products," The Lancet 343:1583-1584.
Thömmes, J. et al. (2009). "Alternatives to Packed-Bed Chromatography for Antibody Extraction and Purification," Chapter 14 in Process Scale Purification of Antibodies, U. Gottschalk (Ed.) pp. 293-308.
Tipton, B. et al. (Sep. 2002). "Retrovirus and Parvovirus Clearance From An Affinity Column Product Using Adsorptive Depth Filtration," BioPharm 15(9):43-50.
Traunecker, A. et al. (1991). "Bispecific Single Chain Molecules (Janusins) Target Cytotoxic Lymphocytes on HIV Infected Cells," EMBO J. 10(12):3655-3659.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
U.S. Appl. No. 61/181,606. (Copy not submitted herewith pursuant to the waiver of 37 C.F.R. § 1.98(a)(2)(iii) issued by the Office dated Sep. 21, 2004).
U.S. Appl. No. 61/231,811.(Copy not submitted herewith pursuant to the waiver of 37 C.F.R. § 1.98(a)(2)(iii) issued by the Office dated Sep. 21, 2004).
U.S. Appl. No. 61/253,438.(Copy not submitted herewith pursuant to the waiver of 37 C.F.R. § 1.98(a)(2)(iii) issued by the Office dated Sep. 21, 2004).
Urakubo, T. et al. (2008). "The Quality Risk Management of Biopharmaceuticals," PDA Journal of GMP and Validation in Japan 10(2):23-26.
Van Reis, R. et al. (2007, e-pub. Mar. 1, 2007). "Bioprocess Membrane Technology," Journal of Membrane Science 297(1-2):16-50.
Verhoeyen, M et al. (Mar. 25, 1988). "Reshaping Human Antibodies: Grafting an Antilysozyme Activity," Science 239:1534-1536.
Viral Safety Evaluation of Biotechnology Products Derived from Cell Lines of Human or Animal Origin, Japan, p. 1-21, Tables 1-4, Appendices 1-5 (Feb. 22, 2000) (in Japanese).
Wahome, J. et al. (May 1, 2008). "Impact of Lot-to-Lot Variability of Cation Exchange Chromatography Resin on Process Performance," Biopharm. Int. 21 (5):1-5.

(56) References Cited

OTHER PUBLICATIONS

Waterhouse, P. et al. (1993). "Combinatorial Infection and in Vivo Recombination: a Strategy for Making Large Phage Antibody Repertoires," Nucl. Acids Res. 21(9):2265-2266.

Written Opinion of The International Searching Authority, dated Nov. 12, 2010, for PCT Application No. PCT/US2010/044760, filed Aug. 6, 2010, 5 pages.

Wurm, F.M. (Nov. 2004, e-pub. Nov. 4, 2004). "Production of Recombinant Protein Therapeutics in Cultivated Mammalian Cells," Nature Biotechnology 22(11):1393-1398.

Zapata, G. et al. (1995). "Engineering Linear F(ab')2 Fragments For Efficient Production In *Escherichia coli* and Enhanced Antiproliferative Activity," Protein Engineering 8(10):1057-1062.

Zhou, J.X. (2009). "Orthogonal Virus Clearance Applications in Monoclonal Antibody Production," Chapter 8 in Process Scale Purification of Antibodies, U. Gottschalk (Ed.), pp. 169-186.

Brown, A. et al. (2010). "Overloading Ion-Exchange Membranes as a Purification Step for Monoclonal Antibodies," Biotechnol. App. Biochem. 56:59-70.

Jayapal, K.P. et al. (2007). "Recombinant Protein Therapeutics From CHO Cells—20 Years and Counting," Chem. Eng. Prog. 103(10):40-47.

Kandula, S. et al. (Aug. 5, 2009). "Design of a Filter Train for Precipitate Removal in Monoclonal Antibody Downstream Processing," Biotechnol. Appl. Biochem 54:149-155.

Knudsen, H.L. et al. (2001). "Membrane Ion-Exchange Chromatorgraphy For Process-Scale Antibody Purification," J. Chrom A 907:145-154.

Nomura, S. et al. (2005). "Separation and Purification Technique by Using Membrane Chromatography 'Mustang®'," PDA Journal of GMP and Validation in Japan 7(1):59-67. English Abstract.

Ritzén, U. et al. (2007, e-pub. Jun. 29, 2007). "Endotoxin Reduction in Monoclonal Antibody Preparations Using Arginine," J. Chromatogr. B. 856:343-347.

Saxena, A. et al. (2008, e-pub. Aug. 5, 2008). "Membrane-Based Techniques For the Separation and Purification of Proteins: An Overview," Adv. Colloid Interface Sci. 145:1-22.

Zhou, J.X. et al. (2006). "Basic Concepts In Q Membrane Chromatography For Large-Scale Antibody Production," Biotechnol. P 22:341-349.

A schematic of the experimental setup used for virus filtration studies.

Effect of sterile and depth filter on the capacity of parvovirus retentive filter. Experiments were performed at pH 5.5 and conductivity of 8.5 mS/cm. mAb concentration was approximately 13 g/L.

Effect of cation-exchange and endotoxin removal media as prefiltration step on the capacity of parvovirus retentive filter. The data in 3A and 3B were generated at pH 5.0 and 6.5 respectively with MAbI.

Effect of a novel prefiltration train containing both cation-exchange and endotoxin removal media on the capacity of parvovirus retentive filter with MAb1. The data in 4A and 4B were generated at pH 5.0 and 6.5 respectively.

Effect of a novel prefiltration train containing both cation-exchange and endotoxin removal media compared to cation-exchange pre-filtration media on the capacity of parvovirus retentive filter with MAb 2.

METHOD TO IMPROVE VIRUS FILTRATION CAPACITY

CROSS-REFERENCE TO RELATED APPLICATIONS

This application is a continuation of U.S. patent application Ser. No. 12/806,171, filed on Aug. 6, 2010, which claims priority under 35 U.S.C. Section 119(e) and the benefit of U.S. Provisional Application No. 61/231,811, filed Aug. 6, 2009, the entire disclosure of which is incorporated herein by reference in its entirety.

BACKGROUND OF THE INVENTION

Field of the Invention

The present invention is from the field of protein purification. In particular, the invention concerns methods for increasing the filtration capacity of virus filters, by combined use of endotoxin removal and cation-exchange media in the prefiltration process.

Description of the Related Art

Mammalian cell lines have become the primary choice for production of recombinant protein therapeutics due to their capacity for proper protein folding and post translational modification such as glycosylation (Chu and Robinson Current Opinion in Biotechnology 12:180-187, 2001). However, these cell lines are also known to contain retrovirus like particles (Lieber et al. Science 182:56-59, 1973; Lubiniecki et al. Dev Biol Stand 70:187-191, 1989) and possess the risk for potential adventitious virus contamination (Garnick, Dev Biol Stand. Basel: Karger 93:21-29, 1998). While the biopharmaceutical industry producing recombinant protein drugs has a good safety record, there have been past incidences of viral infection by blood and blood products derived from plasma (Brown, Dev. Biol. Stand. 81, 1993; Thomas, Lancet 343:1583-1584, 1994). To mitigate the risk of viral contamination during recombinant protein production, downstream purification processes are designed to include process steps that remove endogenous and adventitious viruses. Adequate virus clearance is obtained by a combination of several process steps that provide either virus inactivation or virus removal from the process feed stream. While viral inactivation is achieved using techniques such as incubation at low pH, heat treatment, and detergents, virus removal is typically performed using chromatography and filtration (Curtis et al., Biotechnology and Bioengineering 84(2):179-186, 2003).

Unlike chromatography media, which removes viruses based on physicochemical properties such as net charge, virus filtration removes viruses by size exclusion and is therefore considered a more robust technique. So far usage of virus filtration during downstream purification of biotherapeutics derived from mammalian cell cultures has been limited to removal of retroviruses (80-100 nm diameter) due to lack of high throughput membranes with nominal pore size less than 60 nm.

Recent advances in membrane technology have enabled manufacturing of high throughput membranes with nominal pore size of 20 nm. These virus filters are retentive to parvoviruses (18-26 nm diameter) and allow passage of proteins that are as large as 160 kD (~8 nm), e.g., monoclonal antibodies (mAbs).

The high selectivity and high throughput with parvovirus filters is achieved by casting a thin retentive membrane layer on a microporous substrate. The thin retentive layer while allows very fine separation of proteins and viruses, it is also susceptible to fouling by impurities in the process feedstream resulting in lower filter capacity and flux. The fouling of the virus filters has been attributed to contaminants such as protein aggregates and denatured protein. Bohonak and Zydney (Bohonak and Zydney, Journal of Membrane Science 254(1-2):71-79, 2005) showed that loss in filter capacity could be due to cake formation or pore blockage. Other recent reports (Bolton et al., Biotechnol. Appl. Biochem. 43:55-63, 2006; Levy et al., Filtration in the Biopharamaceutical Industry. (Meltzer, T. H. and Jornitz, M. W., eds.) pp. 619-646, Marcel Dekker, New York, 1998) have attributed the likely cause of filter fouling to the adsorption of impurities to the pore walls. Several publications (Bolton et al., Biotechnology and Applied Biochemistry 42:133-142, 2005; Hirasaki et al., Polymer Journal 26(11):1244-1256, 1994; Omar and Kempf, Transfusion 42(8):1005-1010, 2002) have also demonstrated that reduction in filter capacity or plugging of pores can decrease viral retention by few orders of magnitude, affecting the robustness of the unit operation.

A lot of recent research has thus focused on identification of pre-filters for removing the foulants from the process feedstream to minimize virus filter fouling and ensuring high capacity, high throughput and robust viral retention. Bolton et al. (Bolton et al. 2006) performed a thorough study that involved testing of several membranes as prefilters and demonstrated that it was possible to increase capacity of normal flow parvovirus (NFP) membranes by almost an order of magnitude by using VIRESOLVE™ depth filter as a prefilter. Brown et al. (Brown et al. 2008, *Use of Charged Membranes to Identify Soluble Protein Foulants in order to Facilitate Parvovirus Filtration*. IBC's 20th Antibody Development and Production, San Diego, Calif.) evaluated a strong cation exchange membrane adsorber as a prefilter to parvovirus retentive filter and showed that the capacity of virus filter could be increased by several fold for eleven different mAb streams. The authors hypothesized that the cation exchange membrane adsorber removed large molecular weight (~600-1500 kD) protein aggregates from the feedstream by competitive adsorption, preventing the virus filter from plugging. U.S. Pat. No. 7,118,675 (Siwak et al.) describes a process that utilizes a charge-modified membrane to remove protein aggregates from a protein solution to prevent fouling of virus filter.

SUMMARY OF THE INVENTION

The present invention is based, at least in part, on the experimental finding that fouling of parvovirus filters could be due to impurities other than those mentioned in the literature and more comprehensive prefiltration solutions are required to improve the virus filtration capacity. Accordingly, the present invention provides a novel prefiltration solution that performs significantly better than the best prefiltration approach mentioned in the literature (cation-exchange membrane adsorbers).

In one aspect, the invention concerns a method of improving the filtration capacity of a virus filter during protein purification, comprising subjecting a composition comprising a protein to be purified to a cation exchange step and an endotoxin removal step, in either order, prior to passing through said virus filter.

In one embodiment, the pore size of the virus filter is between about 15 and about 100 nm in diameter.

In another embodiment, the pore size of the virus filter is between about 15 and about 30 nm in diameter.

In yet another embodiment, the pore size of the virus filter is about 20 nm.

In a further embodiment, the virus to be removed is a parvovirus.

In a still further embodiment, the diameter of the parvovirus is between about 18 and about 26 nm.

In a different embodiment, the protein is an antibody or an antibody fragment, such as an antibody produced by recombinant DNA techniques, or a fragment thereof.

In another embodiment, the antibody is a therapeutic antibody.

In yet another embodiment, the recombinant antibody or antibody fragment is produced in a mammalian host cell, such as, for example, a Chinese Hamster Ovary (CHO) cell.

In a further embodiment, the composition comprising the protein to be purified is first subjected to a cation exchange step followed by an endotoxin removal step, prior to virus filtration.

In a still further embodiment, the composition comprising the protein to be purified is first subjected to an endotoxin removal step followed by a cation exchange step, prior to virus filtration.

In another embodiment, the composition comprising the protein to be purified is subjected to a cation exchange step and endotoxin removal step simultaneously, prior to virus filtration, by keeping the two media together in a single module.

In yet another embodiment, the endotoxin removal step is directly followed by virus filtration.

In a further embodiment, the cation exchange step is directly followed by virus filtration.

In a different embodiment, virus filtration is performed at a pH between about 4 and about 10.

In another embodiment, the protein concentration in the composition to be purified is about 1-40 g/L.

In yet another embodiment, the antibody to be purified is to one or more antigens selected from the group consisting of HER1 (EGFR), HER2, HER3, HER4, VEGF, CD20, CD22, CD11a, CD11b, CD11c, CD18, an ICAM, VLA-4, VCAM, IL-17A and/or F, IgE, DR5, CD40, Apo2L/TRAIL, EGFL7, NRP1, mitogen activated protein kinase (MAPK), and Factor D.

In a further embodiment, the antibody is selected from the group consisting of anti-estrogen receptor antibody, anti-progesterone receptor antibody, anti-p53 antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

DETAILED DESCRIPTION OF THE PREFERRED EMBODIMENT

I. Definitions

Figure 1:
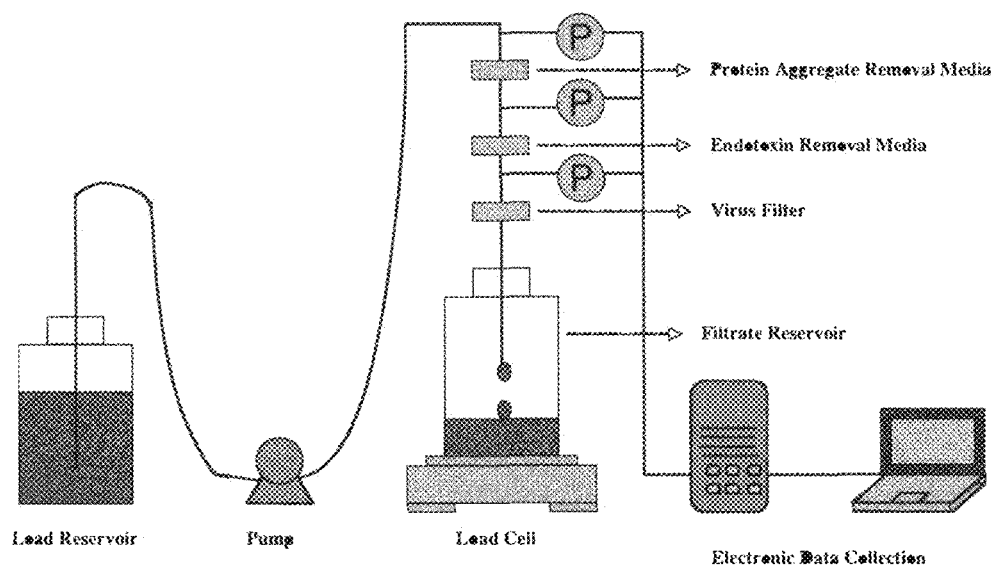
FIG. 1: A schematic of the experimental setup used for virus filtration studies.

By "protein" is meant a sequence of amino acids for which the chain length is sufficient to produce the higher levels of tertiary and/or quaternary structure. Thus, proteins are distinguished from "peptides" which are also amino acid-based molecules that do not have such structure. Typically, a protein for use herein will have a molecular weight of at least about 15-20 kD, preferably at least about 20 kD.

Examples of proteins encompassed within the definition herein include mammalian proteins, such as, e.g., CD4, integrins and their subunits, such as beta7, growth hormone, including human growth hormone and bovine growth hormone; growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or tissue-type plasminogen activator (t-PA, e.g., Activase®, TNKase®, Retevase®); bombazine; thrombin; tumor necrosis factor-α and -β; enkephalinase; RANTES (regulated on activation normally T-cell expressed and secreted); human macrophage inflammatory protein (MIP-1-α); serum albumin such as human serum albumin; mullerian-inhibiting substance; mouse gonadotropin-associated peptide; DNase; inhibin; activin; vascular endothelial growth factor (VEGF); IgE, receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; other CD proteins such as CD3, CD8, CD19 and CD20; erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER1 (EGFR), HER2, HER3 or HER4 receptor; Apo2L/TRAIL, and fragments of any of the above-listed polypeptides; as well as immunoadhesins and antibodies binding to; and biologically active fragments or variants of any of the above-listed proteins.

Specifically included within the definition of "protein," as defined herein, are therapeutic antibodies and immunoadhesins, including, without limitation, antibodies to one or more of the following antigens: HER1 (EGFR), HER2, HER3, HER4, VEGF, CD20, CD22, CD11a, CD11b, CD11c, CD18, an ICAM, VLA-4, VCAM. IL-17A and/or F, IgE, DR5, CD40, Apo2L/TRAIL, EGFL7, NRP1, mitogen activated protein kinase (MAPK), and Factor D, and fragments thereof.

Other exemplary antibodies include those selected from, and without limitation, anti-estrogen receptor antibody, anti-progesterone receptor antibody, anti-p53 antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

An "isolated" protein, such as antibody, is one which has been identified and separated and/or recovered from a component of its natural environment. Contaminant components of its natural environment are materials which would interfere with diagnostic or therapeutic uses for the protein, such as antibody, and may include enzymes, hormones, and other proteinaceous or nonproteinaceous solutes. In preferred embodiments, the protein, such as antibody, will be purified (1) to greater than 95% by weight as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

The protein is preferably essentially pure and desirably essentially homogeneous (i.e. free from contaminating proteins). "Essentially pure" protein means a composition comprising at least about 90% by weight of the protein, based on total weight of the composition, preferably at least about 95% by weight.

"Essentially homogeneous" protein means a composition comprising at least about 99% by weight of protein, based on total weight of the composition.

The term "antibody" is used in the broadest sense and specifically covers monoclonal antibodies (including full length antibodies which have an immunoglobulin Fc region), antibody compositions with polyepitopic specificity, bispecific antibodies, diabodies, and single-chain molecules, as well as antibody fragments (e.g., Fab, F(ab')$_2$, and Fv).

The basic 4-chain antibody unit is a heterotetrameric glycoprotein composed of two identical light (L) chains and two identical heavy (H) chains. An IgM antibody consists of 5 of the basic heterotetramer unit along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and μ classes are further divided into subclasses on the basis of relatively minor differences in the CH sequence and function, e.g., humans express the following subclasses: IgG1, IgG2, IgG3, IgG4, IgA1 and IgA2.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, the V regions consist of relatively invariant stretches called framework regions (FRs) of about 15-30 amino acid residues separated by shorter regions of extreme variability called "hypervariable regions" or sometimes "complementarity determining regions" (CDRs) that are each approximately 9-12 amino acid residues in length. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen binding site of antibodies (see Kabat et al., *Sequences of Proteins of Immunological Interest*, 5th Ed. Public Health Service, National Institutes of Health, Bethesda, Md. (1991). The constant domains are not involved directly in binding an antibody to an antigen, but exhibit various effector functions, such as participation of the antibody dependent cellular cytotoxicity (ADCC).

The term "hypervariable region" (also known as "complementarity determining regions" or CDRs) when used herein refers to the amino acid residues of an antibody which are (usually three or four short regions of extreme sequence variability) within the V-region domain of an immunoglobulin which form the antigen-binding site and are the main determinants of antigen specificity. There are at least two methods for identifying the CDR residues: (1) An approach based on cross-species sequence variability (i.e., Kabat et al., *Sequences of Proteins of Immunological Interest* (National Institute of Health, Bethesda, M S 1991); and (2) An approach based on crystallographic studies of antigen-antibody complexes (Chothia, C. et al., *J. Mol. Biol.* 196: 901-917 (1987)). However, to the extent that two residue identification techniques define regions of overlapping, but not identical regions, they can be combined to define a hybrid CDR.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)).

An "intact" antibody is one which comprises an antigen-binding site as well as a CL and at least the heavy chain domains, $C_H1$, $C_H2$ and $C_H3$.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervarible loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of*

*Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

An antibody "which binds" a molecular target or an antigen of interest is one capable of binding that antigen with sufficient affinity such that the antibody is useful in targeting a cell expressing the antigen.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. In such embodiments, the extent of binding of the antibody to these other polypeptides or polypeptide epitopes will be less than 10%, as determined by fluorescence activated cell sorting (FACS) analysis or radioimmunoprecipitation (RIA), relative to binding to the target polypeptide or epitope.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) of mostly human sequences, which contain minimal sequence derived from non-human immunoglobulin. For the most part, humanized antibodies are human immunoglobulins (recipient antibody) in which residues from a hypervariable region (also CDR) of the recipient are replaced by residues from a hypervariable region of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody optimally also will comprise at least a portion of an immunoglobulin constant region (Fc), typically that of a human immunoglobulin. For further details, see Jones et al., *Nature,* 321:522-525 (1986); Reichmann et al., *Nature,* 332:323-329 (1988); and Presta, *Curr. Op. Struct. Biol.,* 2:593-596 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ACDD assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein. The term also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils, with PBMCs and MNK cells being preferred. The effector cells may be isolated from a native source, e.g., blood.

"Complement dependent cytotoxicity" of "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example using a leucine zipper. Antibody conjugates have another entity, such as a cytotoxic compound, drug, composition, compound, radioactive element, or detectable label, attached to an antibody or antibody fragment.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, non-human higher primates, domestic and farm animals, and zoo, sports, or pet animals, such as dogs, horses, rabbits, cattle, pigs, hamsters, mice, cats, etc. Preferably, the mammal is human.

A "disorder" is any condition that would benefit from treatment with the protein. This includes chronic and acute disorders or diseases including those pathological conditions which predispose the mammal to the disorder in question.

A "therapeutically effective amount" is at least the minimum concentration required to effect a measurable improvement or prevention of a particular disorder. Therapeutically effective amounts of known proteins are well known in the art, while the effective amounts of proteins hereinafter discovered may be determined by standard techniques which are well within the skill of a skilled artisan, such as an ordinary physician.

II. Modes for Carrying Out the Invention

A. Protein Preparation

In accordance with the present invention, the protein is produced by recombinant DNA techniques, i.e., by culturing cells transformed or transfected with a vector containing nucleic acid encoding the protein, as is well known in art.

Preparation of the protein by recombinant means may be accomplished by transfecting or transforming suitable host cells with expression or cloning vectors and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, Ed. (IRL Press, 1991) and Sambrook et al., *Molecular Cloning: A Laboratory Manual*, New York: Cold Spring Harbor Press. Methods of transfection are known to the ordinarily skilled artisan, and include for example, CaPO$_4$ and CaCl$_2$) transfection, electroporation, microinjection, etc. Suitable techniques are also described in Sambrook et al., supra. Additional transfection techniques are described in Shaw et al., *Gene* 23: 315 (1983); WO 89/05859; Graham et al., *Virology* 52: 456-457 (1978) and U.S. Pat. No. 4,399,216.

The nucleic acid encoding the desired protein may be inserted into a replicable vector for cloning or expression. Suitable vectors are publicly available and may take the form of a plasmid, cosmid, viral particle or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, and enhancer element, a promoter, and a transcription termination sequence. Construction of suitable vectors containing one or more of these components employs standard ligation techniques which are known to the skilled artisan.

Forms of the protein may be recovered from culture medium or from host cell lysates. If membrane-bound, it can be released from the membrane using a suitable detergent or through enzymatic cleavage. Cells employed for expression can also be disrupted by various physical or chemical means, such as freeze-thaw cycling, sonication, mechanical disruption or cell lysing agents.

Purification of the protein may be effected by any suitable technique known in the art, such as for example, fractionation on an ion-exchange column, ethanol precipitation, reverse phase HPLC, chromatography on silica or cation-exchange resin (e.g., DEAE), chromatofocusing, SDS-PAGE, ammonium sulfate precipitation, gel filtration using protein A Sepharose columns (e.g., SEPHADEX® G-75) to remove contaminants such as IgG, and metal chelating columns to bind epitope-tagged forms.

B. Antibody Preparation

In certain embodiments of the invention, the protein of choice is an antibody. Techniques for the production of antibodies, including polyclonal, monoclonal, humanized, bispecific and heteroconjugate antibodies follow.

(i) Polyclonal Antibodies.

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (*Goding, Monoclonal Antibodies: Principles and Practice*, pp. 59-103 (Academic Press, 1986).

The immunizing agent will typically include the protein to be formulated. Generally either peripheral blood lymphocytes ("PBLs") are used if cells of human origin are desired, or spleen cells or lymph node cells are used if non-human mammalian sources are desired. The lymphoctyes are then fused with an immortalized cell line using a suitable fusing agent, such as polyethylene glycol, to form a hybridoma cell. Goding, *Monoclonal antibodies: Principles and Practice*, Academic Press (1986), pp. 59-103. Immortalized cell lines are usually transformed mammalian cell, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The immunizing agent will typically include the epitope protein to which the antibody binds. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principals and Practice*, Academic Press (1986), pp. 59-103.

Immortalized cell lines are usually transformed mammalian cells, particularly myeloma cells of rodent, bovine and human origin. Usually, rat or mouse myelome cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies. Kozbor, *J. Immunol.*, 133:3001 (1984); Brodeur et al., *Monoclonal Antibody Production Techniques and Applications*, Marcel Dekker, Inc., New York, (1987) pp. 51-63.

The culture medium in which the hybridoma cells are cultured can then be assayed for the presence of monoclonal antibodies directed against the protein to be formulated. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In a further embodiment, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(iii) Humanized and Human Antibodies.

The antibodies subject to the formulation method may further comprise humanized or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.,* 151:2296 (1993); Chothia et al., *J. Mol. Biol.,* 196:901 (1987). Another method uses a particular framework derived from the consensus sequence of all human antibodies of a particular subgroup of light or heavy chains. The same framework may be used for several different humanized antibodies. Carter et al., *Proc. Natl. Acad. Sci. USA,* 89:4285 (1992); Presta et al., *J Immunol.,* 151:2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993). Human antibodies can also be derived from phage-display libraries (Hoogenboom et al., *J Mol. Biol.,* 227:381 (1991); Marks et al., *J. Mol. Biol.,* 222:581-597 (1991)).

Human antibodies can also be produced using various techniques known in the art, including phage display libraries. Hoogenboom and Winter, *J. Mol. Biol.* 227: 381 (1991); Marks et al., *J. Mol. Biol.* 222: 581 (1991). The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., *J Immunol.* 147(1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resemble that seen in human in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

(iv) Antibody Dependent Enzyme-Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such as way so as to convert it into its more active, cytotoxic form.

Enzymes that are useful in the method of this invention include, but are not limited to, glycosidase, glucose oxidase, human lysozyme, human glucuronidase, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug 5-fluorouracil; proteases, such as serratia protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin Vamidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes" can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the anti-IL-17 or anti-LIF antibodies by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g. Neuberger et al., *Nature* 312: 604-608 (1984)).

(iv) Bispecific and Polyspecific Antibodies

Bispecific antibodies (BsAbs) are antibodies that have binding specificities for at least two different epitopes. Such antibodies can be derived from full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities. Millstein et al., *Nature,* 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions, and, if desired, the immunoglobulin light chain, are inserted into separate expression vectors, and are co-transfected into a suitable host organism. For further details of generating bispecific antibodies, see, for example, Suresh et al., *Methods in Enzymology* 121: 210 (1986).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690, published Mar. 3, 1994. For further details of generating bispecific antibodies see, for example, Suresh et al., Methods in Enzymology, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. For example, Fab' fragments recovered from *E. coli* can be chemically coupled in vitro to form bivalent antibodies. See, Shalaby et al., *J Exp. Med.*, 175:217-225 (1992).

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J Immunol.*, 152:5368 (1994).

Antibodies with more than two valencies are contemplated. For example, trispecific antibodies can be prepared. Tutt et al., *J Immunol.* 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibiotics may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

(v) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells, U.S. Pat. No. 4,676,980, and for treatment of HIV infection. WO 91/00360, WO 92/200373 and EP 03089. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

C. Purification of the Proteins, Including Antibodies

When the target polypeptide is expressed in a recombinant cell other than one of human origin, the target polypeptide is completely free of proteins or polypeptides of human origin. However, it is necessary to purify the target polypeptide from recombinant cell proteins or polypeptides to obtain preparations that are substantially homogeneous as to the target polypeptide. As a first step, the culture medium or lysate is typically centrifuged to remove particulate cell debris. The membrane and soluble protein fractions are then separated. The target polypeptide may then be purified from the soluble protein fraction and from the membrane fraction of the culture lysate, depending on whether the target polypeptide is membrane bound. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Most companies currently producing monoclonal antibodies (MAbs) use a three-column platform approach comprising Protein A affinity chromatography for product capture, followed by anion exchange chromatography in flow-through mode to extract negatively charged contaminants such as host cell protein (HCP), endotoxins, host DNA, and leached Protein A, and then cation exchange chromatography or hydrophobic interaction chromatography (HIC) in retention mode to remove positively charged contaminant species including residual HCP and product aggregates.

Those viruses that may be present in protein solutions are larger than the proteins themselves. It is thus presumed that viruses can be removed from proteins in accordance with size, by filtration.

Virus filtration can remove larger, e.g., retroviruses (80-100 nm diameter), typically using high throughput membranes with nominal pore size of about 60 nm. Since high throughput membranes with nominal pore size of 20 nm are also commercially available, it is possible to remove smaller viruses by filtration, such as, for example, parvoviruses (18-26 nm diameter), while allowing passage of proteins that are as large as 160 kD (~8 nm), e.g., monoclonal antibodies. The present invention is primarily intended for resolving issues typically associated with the filtration of such smaller viruses, using viral removal filters of smaller pore size.

Typically, a virus filtration step can be implemented at any one of several points in a given downstream process. For example, in a typical monoclonal antibody purification process, virus filtration may take place following a low pH viral inactivation step, or following an intermediate column chromatography step, or after a final column chromatography step.

According to the invention, virus filtration unit operation could be carried out at any stage in the downstream process. Virus filtration during downstream processing of monoclonal antibody is typically performed after an affinity chromatography step (capture step) and an ion-exchange purification step (polishing step).

The experimental setup used in the experiments disclosed herein is illustrated in FIG. 1. It is emphasized, however, that the invention is not so limited. Other arrangements, well known in the art, are also suitable and can be used in the methods of the present invention.

In tangential flow virus filtration, the protein solution is usually pumped around at a constant rate of flow on the retention side. The differential pressure generated across the virus removal filter, allows protein solution to permeate through the filter while the viruses are retained on the retentate side.

In the case of so called "normal-flow" or "dead-end" virus filtration, the same virus filter as that used in tangential virus filtration can be used, although the peripheral equipment and operating procedures are much simpler and less expensive than in the case of tangential flow virus filtration. Thus, in principle, "normal-flow" filtration involves placing the macromolecule-containing solution in a pressure vessel prior to filtration and pressing the solution through the virus removal filter with the aid of a pressure source, suitably nitrogen (gas) or air. Alternatively, a pump could be used on the retentate side to filter the liquid through the virus removal filter at a pre-determined flow rate.

The degree of fineness of filters generally, is normally expressed as pore size or the approximate molecular weight (relative molecular mass) at which the molecules are stopped by the filter, the so called cut-off.

Virus filters are known in the art and are supplied by Millipore from Massachusetts, USA and Asahi Chemical Industry Co., Ltd. from Japan, among others. Suitable parvovirus retentive filters include VIRESOLVE® Pro (Millipore Corp., Billerica, Mass.) VIRESOLVE® Pro membrane has an asymmetric dual layer structure and is made from polyethersulfone (PES). The membrane structure is designed to retain viruses greater than 20 nm in size while allowing proteins of molecular weight less than 180 kDa to permeate through the membrane. Other filters suitable for the removal of small viruses, including parvoviruses, from protein solutions include NOVASIP™ DV20 and DV50 Virus Removal Filter Capsules (Pall Corp., East Hills, N.Y.), VIROSART® CPV, Planova 20 N (Asahi Kasei) and BioEX (Asahi Kasei). The NOVASIP™ DV20 grade capsule filter utilizes an ULTIPOR® VF-grade DV20 grade pleated membrane cartridge to remove parvoviruses and other viruses as small as 20 nm from protein solutions up to 5-10 liters. The NOVASIP™ DV50 grade capsule filter incorporates an ULTIPOR® VF DV50 grade ULTIPLEAT® membrane cartridge for removal of viruses 40-50 nm and larger. NOVASIP® ULTIPOR® VF capsule filters are supplied non-sterile and can also be Gamma-irradiated. VIROSART® CPV utilizes double-layer polyethersulfone asymmetric membrane and retains more than 4 log of parvoviruses and 6 log of retroviruses.

Prefiltration of the feed solution can have a dramatic impact on filter performance. Prefiltration typically is targeted to remove impurities and contaminants that might lead to fouling of virus filters, such as protein aggregates, DNA and other trace materials.

According to the present invention, a striking enhancement of the efficacy of virus filters can be achieved by a prefiltration step including the use of both cation exchange and endotoxin removal media. In this context, the term "medium" or "media" is used to cover any means for performing the cation exchange and endotoxin removal steps, respectively. Thus, the term "cation exchange medium" specifically includes, without limitation, cation exchange resins, matrices, absorbers, and the like. The term "endotoxin removal medium" includes, without limitation, any positively charged membrane surface, including, for example, chromatographic endotoxin removal media, endotoxin affinity removal media, and the like.

Cation exchange media suitable for use in the prefiltration step of the present invention include, without limitation, MUSTANG® S, SARTOBIND® S, VIRESOLVE® Shield, SPFF, SPXL, CAPTO® S, POROS® 50 HS, FRACTOGEL® S, HYPERCEL® D etc., which are commercially available.

Endotoxin removal media suitable for use in the prefiltration step of the present invention include, without limitation, MUSTANG® E, MUSTANG® Q, SARTOBIND® Q, CHROMASORB®, POSSIDYNE®, CAPTO® Q, QSFF, POROS® Q, FRACTOGEL® Q etc., which are commercially available.

The pre-filtration step can be performed, for example, by taking the in process chromatography pool and processing the pool over a filtration train that comprises the endotoxin removal and cation exchange media and parvovirus filter. The endotoxin removal and cation exchange media act as pre-filtration steps and the capacity of parvovirus filter is independent of the sequence of two steps in the filtration train. The filtration train can work continuously as a single step or it can be operated as different unit operations. For example, in one embodiment, the chromatography pool is first processed over endotoxin removal media, the collected pool is then processed over cation exchange media and the subsequent pool is filtered with parvovirus filter. As mentioned above, the order of applying the cation exchange media and endotoxin removal media in the process sequence does not impact parvovirus filtration capacity. The process can be operated over a wide pH range, such as, for example, in the pH range of 4-10, with optimal filter capacity being dependent on the target impurity profile and product attributes. Similarly, protein concentrations can vary over a wide range, such as, for example, 1-40 g/L, and does not limit the mass throughput of parvovirus filters.

The invention will be more fully understood by reference to the following examples. They should not, however, be construed as limiting the scope of the invention. All citations throughout the disclosure are hereby expressly incorporated by reference.

EXAMPLE

Materials and Methods

1. Protein Solution

Since virus filtration during downstream processing of monoclonal antibody is performed after the affinity chromatography (capture step) and an ion-exchange step (polishing step), all filtration experiments were performed with commercially relevant in process ion exchange (cation or anion-exchange) chromatography pools. The mAb concentration and pool conductivity for cation exchange and anion exchange pools were respectively 10 mg/ml and 10 mS/cm and 8 mg/ml and 4 ms/cm. Filtration experiments were performed either with fresh feedstock (used within 24 hours of production) or with feedstock that was frozen at −70° C. after production and was thawed at 4-8° C. prior to use. No significant difference was seen in results obtained with fresh or freeze-thawed feedstock. Protein concentration was determined using a UV-vis spectrophotometer (NanoDrop ND-1000, NanoDrop Technologies, Wilmington, Del.) with absorbance measured at 280 nm.

2. Membranes

Filtration experiments were performed with VIRESOLVE® Pro (Millipore Corp., Billerica, Mass.) parvovirus retentive filter. VIRESOLVE® Pro membrane has an asymmetric dual layer structure and is made from polyethersulfone (PES). The membrane structure is designed to retain viruses greater than 20 nm in size while allowing proteins of molecular weight less than 180 kDa to permeate through the membrane. Prefilters to VIRESOLVE® Pro evaluated in this study included VIRESOLVE® Optiscale 40 depth filter (Millipore Corp., Billerica, Mass.), FLUORODYNE® EX Mini 0.2 μm sterile filter (Pall Corp., East Hills, N.Y.) and the membrane adsorbers from MUSTANG® family (Pall Corp., East Hills, N.Y.). The membrane adsorbers were procured from the vendor in fully encapsulated ACRODISC® units. Table 1 summarizes the key properties (functional group, bed volume, pore size etc.) of all the pre-filters used in this study.

TABLE 1

Key Properties of Prefilters

| Prefilter | Utility | Base Matrix | Functional Group | Bed Volume/ Surface Area | Pore Size |
|---|---|---|---|---|---|
| VIRESOLVE ® | Depth Filter | Diatomaceous Earth | — | — | — |
| FLURODYNE ® EX | Sterile Filter | Polyether sulfone | — | 3.8 cm2 | 0.2 μm |
| MUSTANG ® S | Strong Cation Exchanger | Polyether sulfone | Sulfonic Acid | 0.18 ml | 0.8 μm |
| MUSTANG ® Q | Strong Anion Exchanger | Polyether sulfone | Quaternary Amine | 0.18 ml | 0.8 μm |
| MUSTANG ® E | Endotoxin Removal | Polyether sulfone | Polyethylene Imine | 0.12 ml | 0.2 μm |

3. Experimental Setup

Filtration experiments were performed with a custom-built apparatus shown in FIG. 1. The load material, i.e., in process mAb pool, was placed in the load reservoir and was filtered through a filtration train consisting of different combinations of pre-filters and commercially available parvovirus filters. In all filtration experiments, the constant filtration flow rate ($P_{max}$) method was used. Pressure transducers were placed upstream of each filter and were coupled to a Millidaq or a Netdaq system to record differential pressure data as a function of time or mass throughput. Filtrate from the parvovirus filter was collected in a reservoir, which was kept on a load cell to record mass throughput as a function of time.

Results and Discussion

Downstream purification of mAbs expressed in mammalian cell cultures typically utilize centrifugation and depth filtration as a first step to remove cells and cell debris, followed by affinity chromatography for mAb capture and removal of host cell proteins (HCP), followed by cation exchange chromatography, virus filtration, and anion exchange chromatography for further removal of impurities such as aggregates, viruses, leached protein A and HCP's. Majority of the experiments in this study were performed with cation exchange pool with cation exchange chromatography being the second chromatography step.

Figure 2:
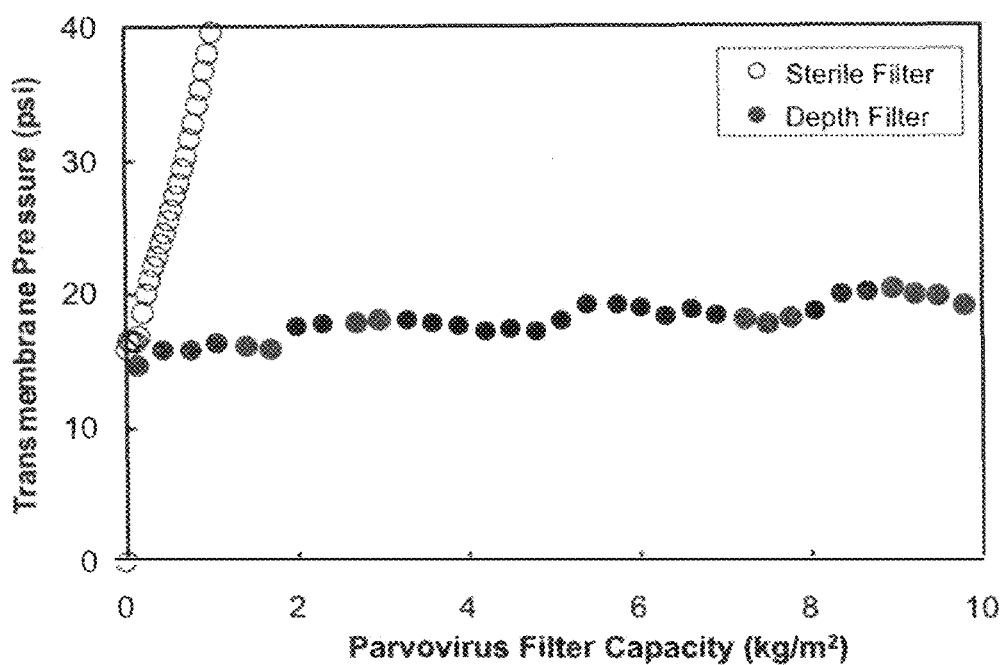
FIG. 2: Effect of sterile and depth filter on the capacity of Viresolve Pro parvovirus retentive filter. Experiments were performed at pH 5.5 and conductivity of 8.5 mS/cm. mAb concentration was approximately 13 g/L.

FIG. 2 shows the experimental data for differential pressure across Viresolve Pro at a constant flux of 200 L/m²/hr with a therapeutic mAb feed stream with different prefilters. X-axis represents the mass of mAb loaded per square meter of virus filter. Y-axis represents the differential pressure across the virus filter as a function of mass throughput. The data clearly indicates that the depth filter provides several orders of magnitude increase in virus filtration capacity compared to sterile filter. Similar observations were made by Bolton et al. (Bolton et al. Appl. Biochem. 43:55-63, 2006) when evaluating the effect of VIRESOLVE Prefilter™—a depth filter media—as a pre-filter to NFP parvovirus retentive filter (Millipore Corp.) with a polyclonal IgG solution. The authors attributed the increase in capacity to the selective adsorption of foulant—denatured protein—due to hydrophobic interactions.

Although depth filters have traditionally been used successfully for clarification of cell culture fluid, there are quite a few limitations that deserve extra consideration when used downstream of capture steps, e.g., as a prefilter to parvovirus retentive filter.
  (a) Depth filters are not base stable which prevents the sanitization of process train after installation, resulting in open processing and potential for bioburden growth.
  (b) Composition of depth filters includes diatomaceous earth as a key component, which is typically food grade and presents quality concerns.
  (c) The diatomaceous earth is generally sourced from nature—lacking a well defined chemical process—and can thus can have lot to lot variations.
  (d) Depth filters also tend to leach metals, beta-glycans and other impurities, the clearance of which needs to be demonstrated and validated with downstream operations.

These limitations put extra burden on process development as the unit operations downstream of depth filter would have to be designed to provide adequate clearance of leachables. However, even if the requisite of leachable clearance was met, there are reasons to be concerned that a particular lot of depth filter may have significantly higher leachables than what the process is capable of clearing as the key components are sourced from nature, that is, they lack a well defined chemical synthesis process.

Figure 3A:
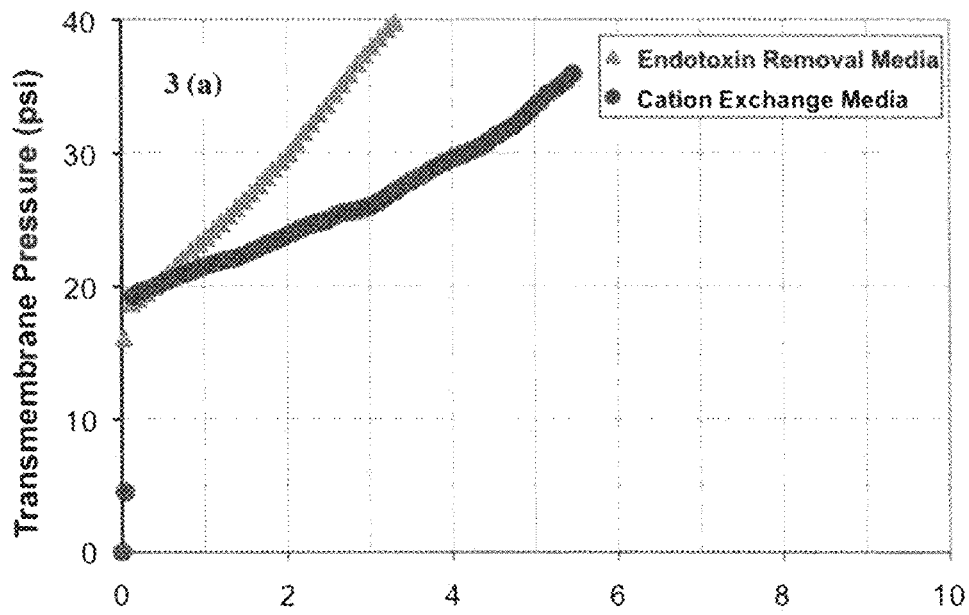
FIGS. 3 (a) and (b): Effect of cation-exchange and endotoxin removal membrane adsorbers as prefilters on the capacity of Viresolve Pro parvovirus filter. The data in 3 (a) and 3 (b) were generated at pH 5.0 and 6.5 respectively with MAb1.
Figure 3B:
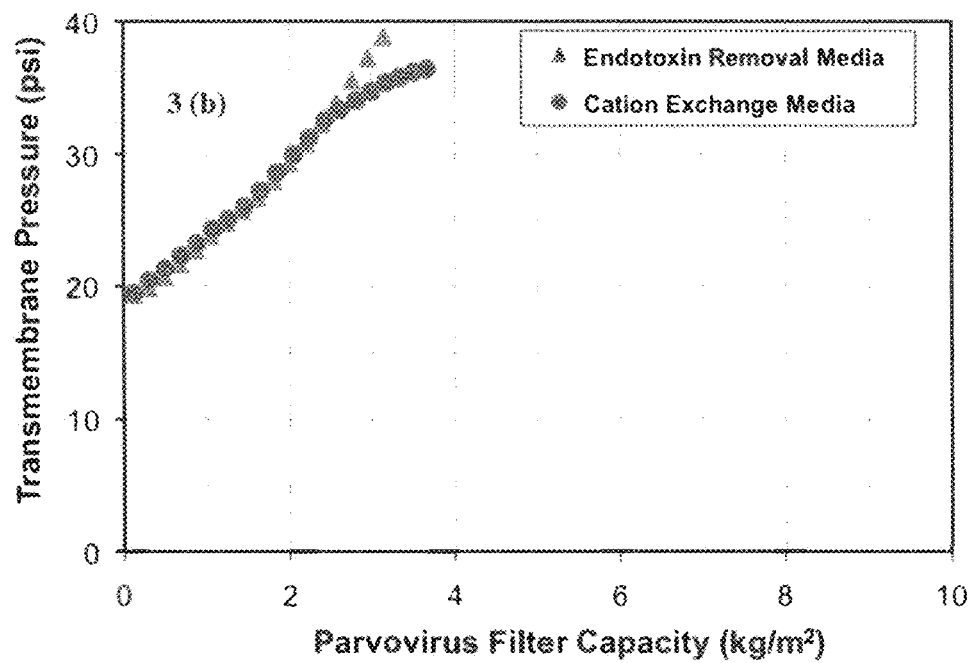

There has thus been a significant interest in development of pre-filters that do not present these limitations. As mentioned above, Brown et al. (Brown et al. IBC's 20$^{th}$ Antibody Development and Production, San Diego, Calif., 2008) recently showed that Mustang S, a strong negatively charged ion-exchanger, when used as a prefilter could increase the capacity of parvovirus retentive filter by several fold. Experiments were thus conducted to evaluate the effect of different prefiltration media to Viresolve® Pro. The experimental data at pH 5.0 and 6.5 is shown in FIGS. 3 (a) & (b). The data shows that while cation exchange media shows slight benefit over endotoxin removal adsorber at pH 5.0, the benefit disappeared at pH 6.5. While the overall capacities with both media were higher than those with sterile filter (FIG. 2); they were nonetheless significantly short of the capacity required to successfully conduct the unit operation at manufacturing scale.

Figure 4A:
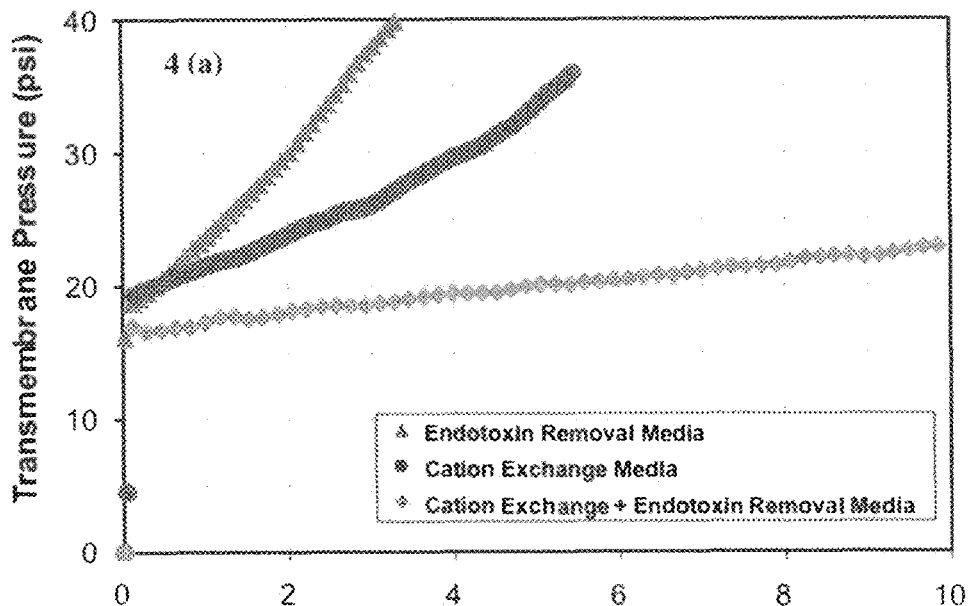
FIGS. 4 (a) and (b): Effect of a novel prefiltration train containing both cation-exchange and endotoxin removal membrane adsorbers on the capacity of Viresolve Pro parvovirus retentive filter with MAb1. The data in 4 (a) and 4 (b) were generated at pH 5.0 and 6.5 respectively.
Figure 4B:
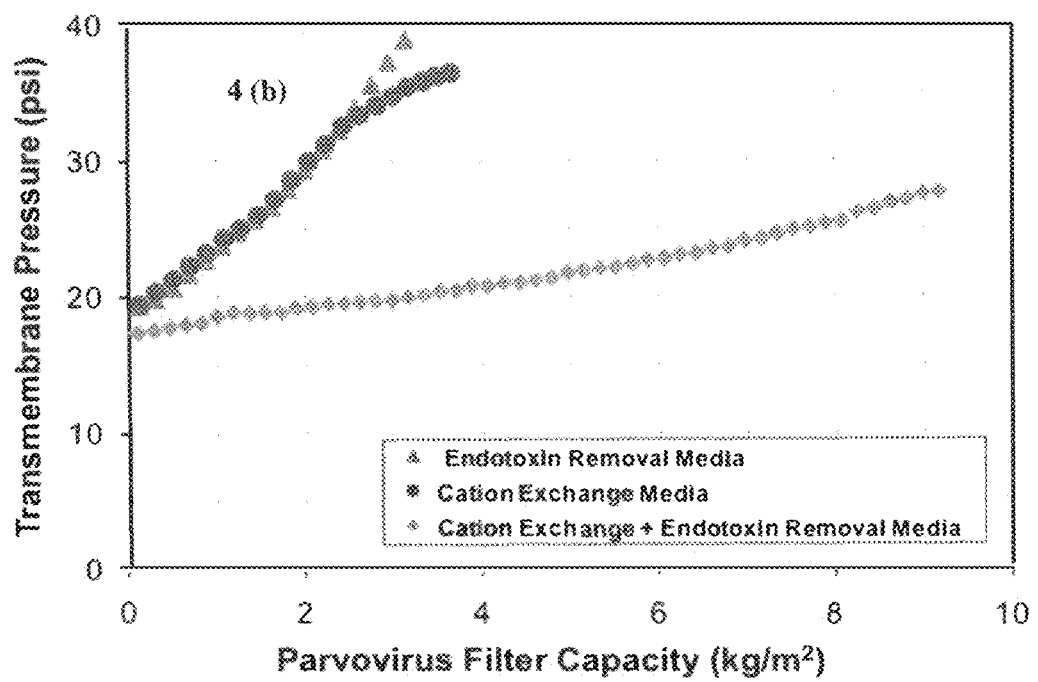

Based on the hypothesis that both cation exchange and endotoxin removal media could be removing two different foulants; both of which may lead to filter fouling, an experiment was designed with a novel prefiltration train that included both cation exchange and endotoxin removal media. Experimental results are shown in FIGS. 4 (a) and (b) at pH 5.0 and pH 6.5 respectively. The data clearly indicate that the combination of two media is significantly better than each of the media by itself. For example, at pH 5.0, the combination of cation exchange and endotoxin removal media provide greater than an order of magnitude improvement in capacity at 20 psi differential pressure. While similar trend was also seen at pH 6.5, the overall capacity was lower than that obtained at pH 5.0. It could be due to more robust removal of impurities at lower pH.

Figure 5:
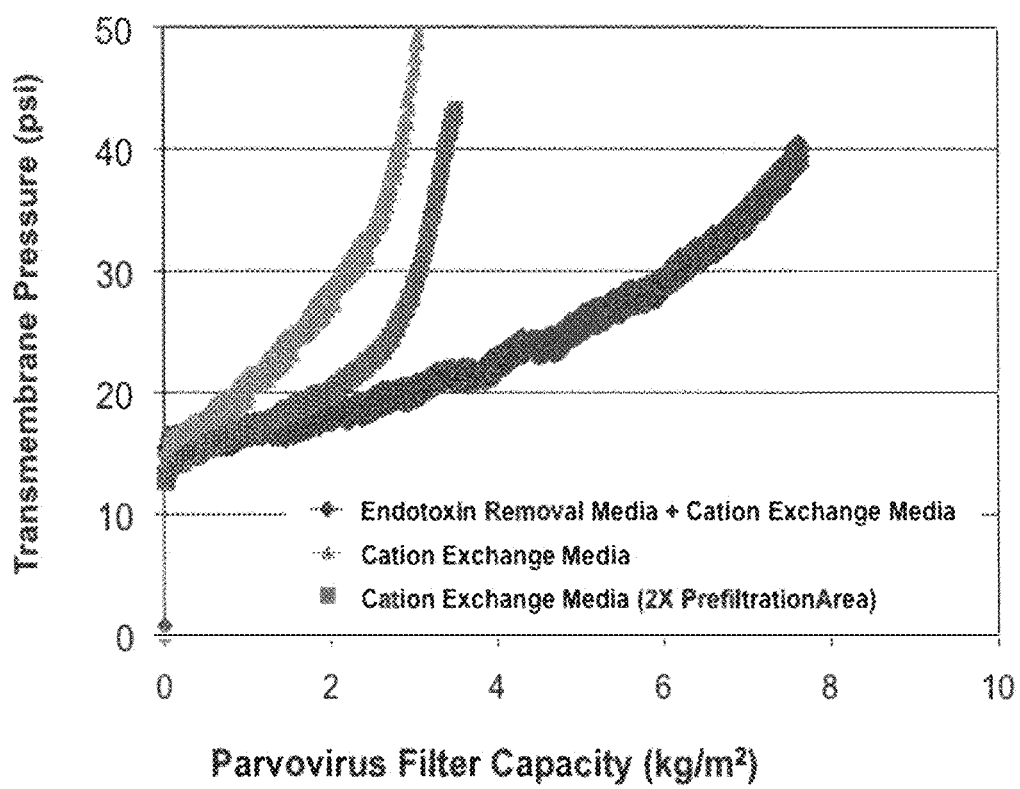
FIG. 5: Effect of a novel prefiltration train containing both cation-exchange and endotoxin removal membrane adsorbers compared to cation-exchange pre-filtration media on the capacity of parvovirus retentive filter with MAb2.

Experimental results with MAb2 are shown in FIG. 5. Consistent with data in FIG. 4, the novel prefiltration train containing both endotoxin removal media and cation exchange media increased the capacity substantially, suggesting that endotoxin removal media and cation exchange media work synergistically and remove two different classes of foulants.

CONCLUSIONS

Majority of the previous work has focused on the use of depth filters or cation exchange membrane adsorbers as prefilters to increase the capacity of parvovirus retentive filters. While depth filters provide a robust mechanism for increasing virus filtration capacity, limitations associated with them such as leachables limit their application to a specific stage in the downstream purification sequence. While cation-exchange membrane adsorbers may increase the parvovirus filter capacity for some monoclonal antibody (mAb) feedstreams, they may not be universally applicable as seen with the data in this study, suggesting that there may be multiple foulants present, which need to be addressed to further improve performance of parvovirus removal filters.

The present invention, as demonstrated by the above experimental results, highlights two aspects—(1) Endotoxin removal media by itself can effectively increase the capacity of parvovirus filters when used for prefiltration and (2) coupling of endotoxin removal and cation exchange media in the prefiltration train can provide several-fold increase in parvovirus filtration capacity, lowering raw material costs and facilitating successful operation of virus filtration at manufacturing scale.

What is claimed is:

1. A method of improving the filtration capacity of a virus filter during protein purification, comprising subjecting a composition comprising a protein to be purified to a cation exchange step and an endotoxin removal step, in either order, prior to passing through said virus filter,
  wherein the protein to be purified is a therapeutic monoclonal antibody or a fragment thereof,
  wherein the composition to be purified is an ion exchange chromatography pool,
  wherein the virus filter is a parvovirus filter, and
  wherein in the cation exchange step the composition is processed over a cation exchange membrane adsorber and in the endotoxin removal step the composition is processed over an endotoxin removal membrane adsorber.

2. The method of claim 1 wherein the pore size of the virus filter is between about 15 and about 100 nm diameter.

3. The method of claim 2 wherein the pore size of the virus filter is between about 15 and about 30 nm diameter.

4. The method of claim 3 wherein the pore size of the virus filter is about 20 nm.

5. The method of claim 3 wherein the virus to be removed is a parvovirus.

6. The method of claim 5 wherein the diameter of the parvovirus is between about 18 and about 26 nm.

7. The method of claim 1 wherein the therapeutic monoclonal antibody or antibody fragment is produced in a mammalian host cell.

8. The method of claim 7 wherein the mammalian host cell is a Chinese Hamster Ovary (CHO) cell.

9. The method of claim 1 wherein the composition comprising the protein to be purified is first subjected to the cation exchange step followed by the endotoxin removal step, prior to virus filtration.

10. The method of claim 1 wherein the composition comprising the protein to be purified is first subjected to the endotoxin removal step followed by the cation exchange step, prior to virus filtration.

11. The method of claim 1 wherein the composition comprising the protein to be purified is subjected to the endotoxin removal step and the cation exchange step simultaneously, prior to virus filtration.

12. The method of claim 9 wherein said endotoxin removal step is directly followed by virus filtration.

13. The method of claim 10 wherein said cation exchange step is directly followed by virus filtration.

14. The method of claim 11 wherein said simultaneous endotoxin removal and cation exchange step are directly followed by virus filtration.

15. The method of claim 1 wherein virus filtration is performed at a pH between about 4 and about 10.

16. The method of claim 1 wherein the protein concentration in said composition is about 1-40 g/L.

17. The method claim 1 wherein said therapeutic monoclonal antibody or fragment thereof is to one or more antigens selected from the group consisting of HER1 (EGFR), HER2, HER3, HER4, VEGF, CD20, CD22, CD11a, CD11b, CD11c, CD18, an ICAM, VLA-4, VCAM, IL-17A and/or F, IgE, DR5, CD40, Apo2L/TRAIL, EGFL7, NRP1, mitogen activated protein kinase (MAPK), and Factor D.

18. The method of claim 1 wherein the therapeutic monoclonal antibody or fragment thereof is selected from the group consisting of anti-estrogen receptor antibody, anti-progesterone receptor antibody, anti-p53 antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

* * * * *